United States Patent [19]
Eld

[11] Patent Number: 5,545,141
[45] Date of Patent: Aug. 13, 1996

[54] PERCUTANEOUS GASTROSTOMY FEEDING TUBE APPLICATOR AND METHOD.

[76] Inventor: Larry A. Eld, 3435 N. Cole Rd., Boise, Id. 83704

[21] Appl. No.: 270,229

[22] Filed: Jul. 1, 1994

Related U.S. Application Data

[63] Continuation-in-part of Ser. No. 68,905, May 28, 1993, abandoned.

[51] Int. Cl.⁶ .................................................. A61M 5/178
[52] U.S. Cl. .......................... 604/164; 604/51; 604/264; 606/182
[58] Field of Search .................................. 604/24, 44, 51, 604/93, 95, 164, 175, 264; 606/182

[56] References Cited

U.S. PATENT DOCUMENTS

| | | | |
|---|---|---|---|
| 4,573,576 | 3/1986 | Krol | 206/471 |
| 4,601,710 | 7/1986 | Moll | 604/165 |
| 4,762,519 | 8/1988 | Frimberger | 604/164 |
| 4,826,481 | 5/1989 | Sacks et al. | 604/164 |
| 4,897,081 | 1/1990 | Poirier et al. | 604/175 |
| 5,007,900 | 4/1991 | Picha et al. | 604/106 |
| 5,112,310 | 5/1992 | Grobe | 604/175 |
| 5,152,749 | 10/1992 | Giesy et al. | 604/164 |
| 5,167,627 | 12/1992 | Clegg et al. | 604/164 |

FOREIGN PATENT DOCUMENTS

| | | | |
|---|---|---|---|
| 3345612.7 | 6/1985 | Germany. | |
| 3919740.9 | 12/1990 | Germany. | |
| 2103936 | 8/1981 | United Kingdom | 604/280 |

OTHER PUBLICATIONS

*Enteral Feeding of Critically Ill Pets: The Choices and Techniques*, by P. Jane Armstrong, DVM, MS, Dipl. ACVIM, Dept. Small Animal Clinical Sciences, College of Veterinary Medicine, University of Minnesota, St. Paul, Minnesota 55108, "Symposium on Nutrition and Dietetics", Veterinary Medicine, Sep., 1992.

*Primary Examiner*—John G. Weiss
*Attorney, Agent, or Firm*—Frank J. Dykas

[57] ABSTRACT

Various embodiments of a gastrostomy method and applicator device are shown and described. The gastrostomy device has an elongated body for insertion into the patient's stomach, a removable for piercing a channel through the stomach and abdomen walls, a shield means for removably covering the needle as it is inserted into the stomach, and an actuating means for moving the needle forward to pierce the channel. The gastrostomy method includes piercing the channel from the inside of the stomach to the outside of the patient's body. The method includes insertion of the invented device into the stomach, placement of the needle, unshielding the needle, and actuating the needle to pierce the channel. Optionally, the method may include steps of drawing a strand through the channel and out the mouth, attachment to a feeding tube, and drawing the feeding tube into the stomach and into the channel.

19 Claims, 6 Drawing Sheets

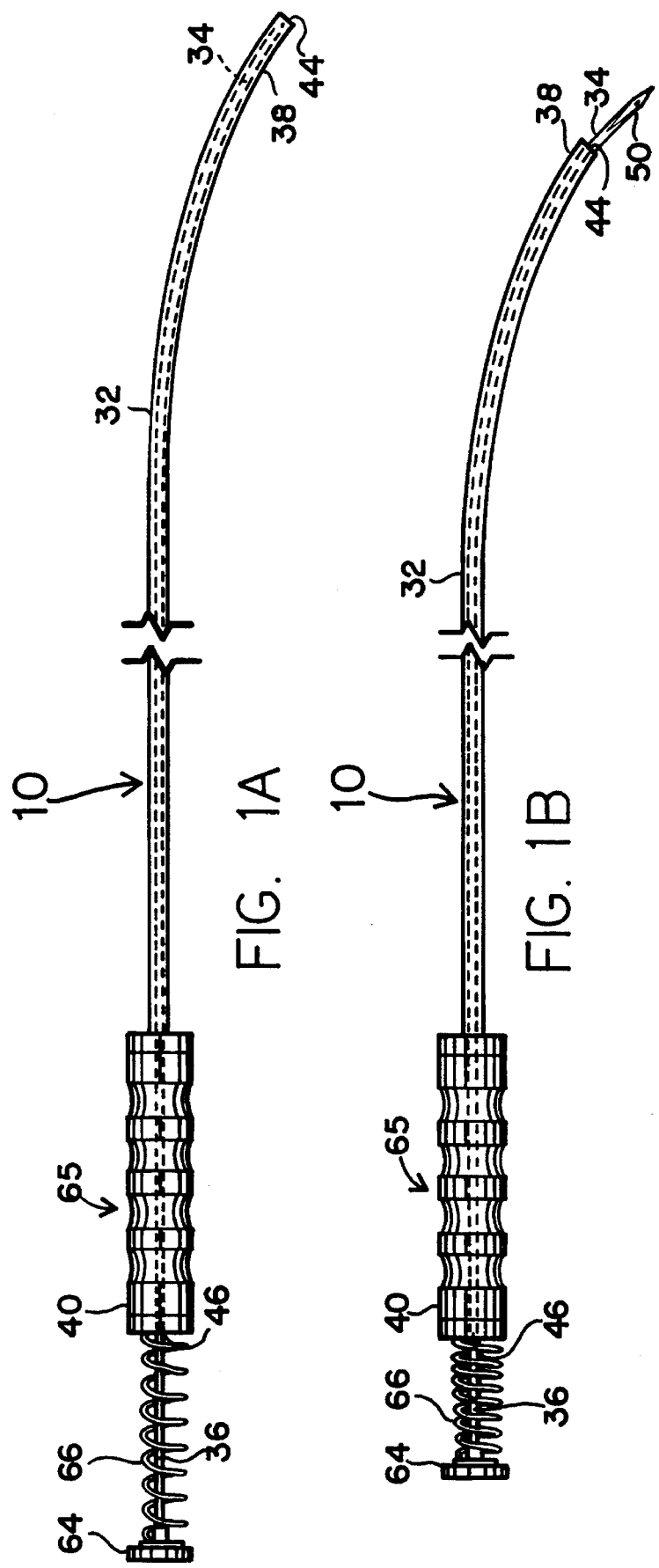

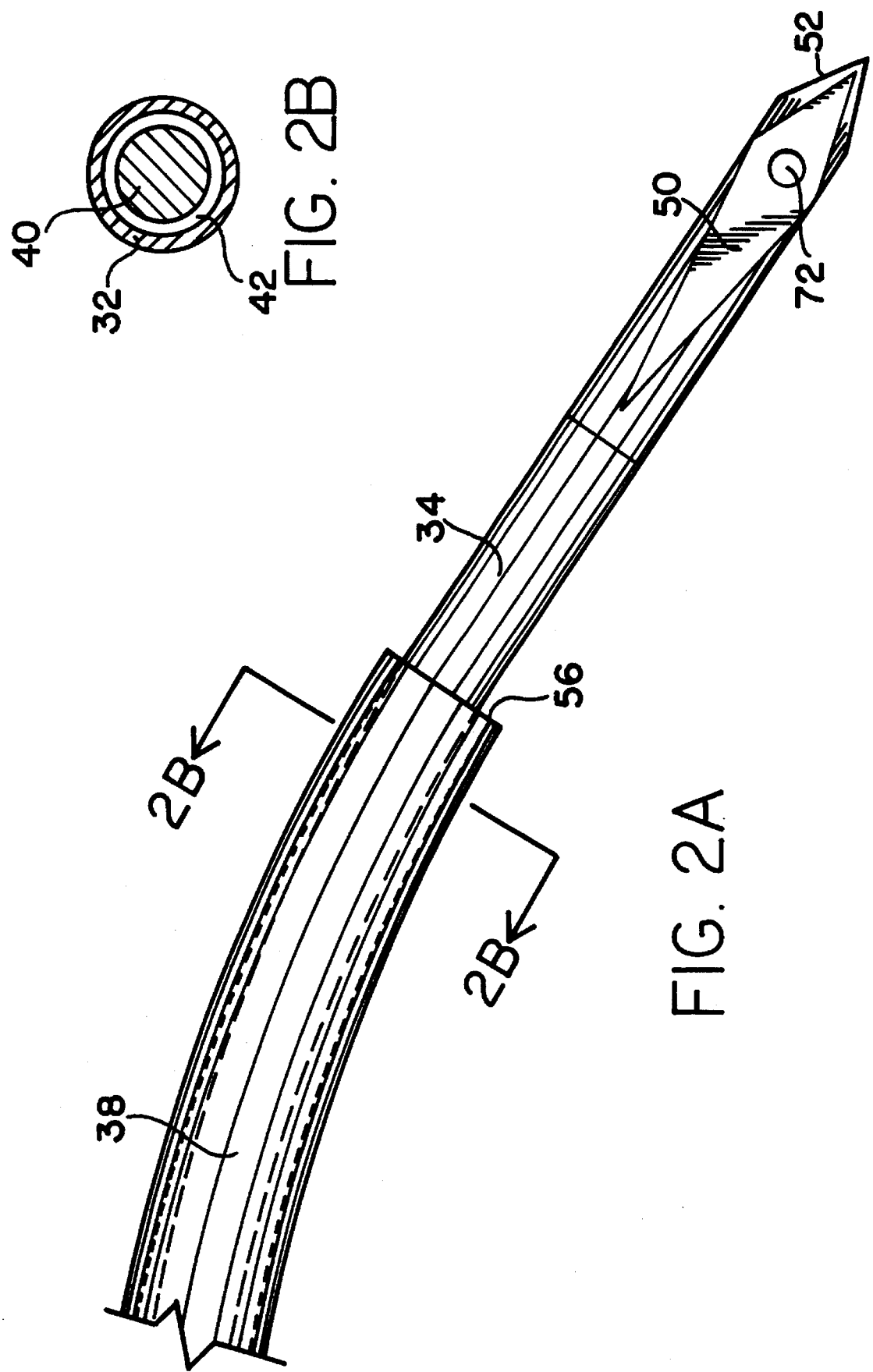

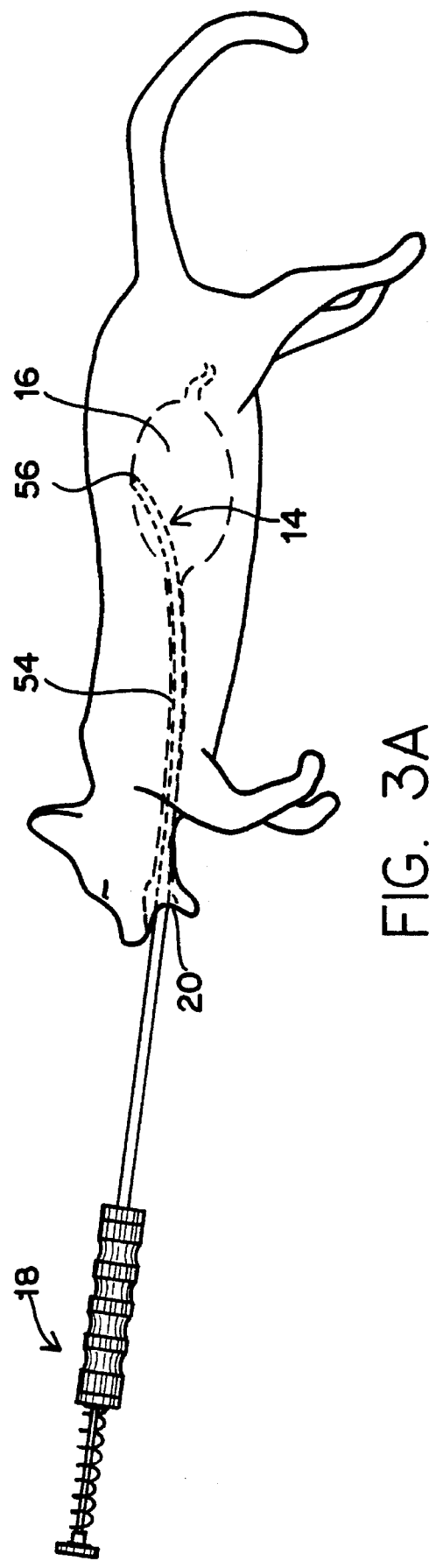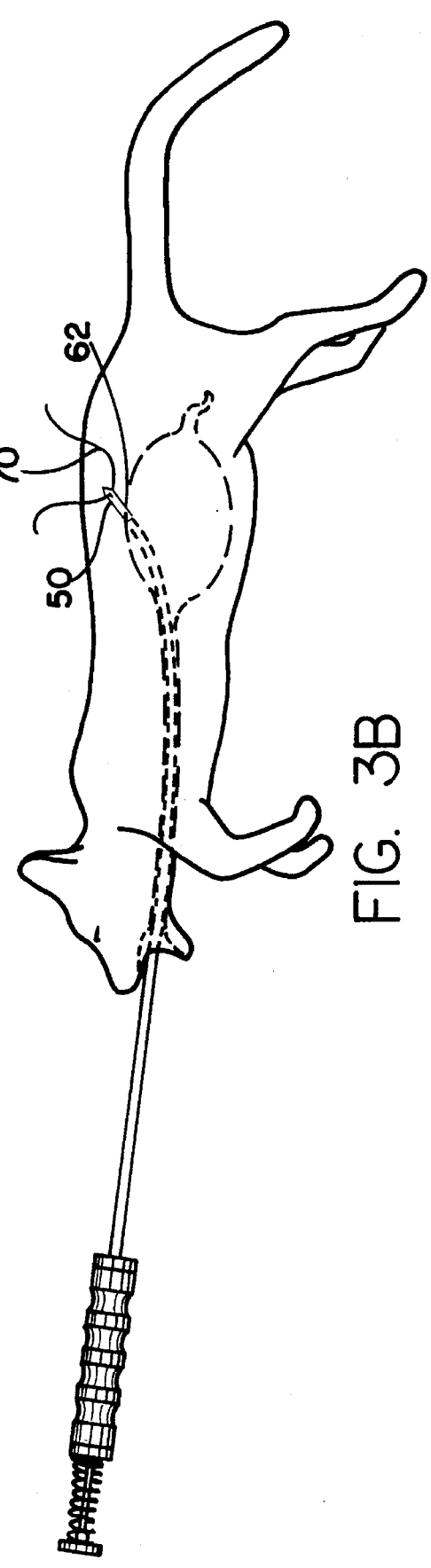
FIG. 3A
FIG. 3B

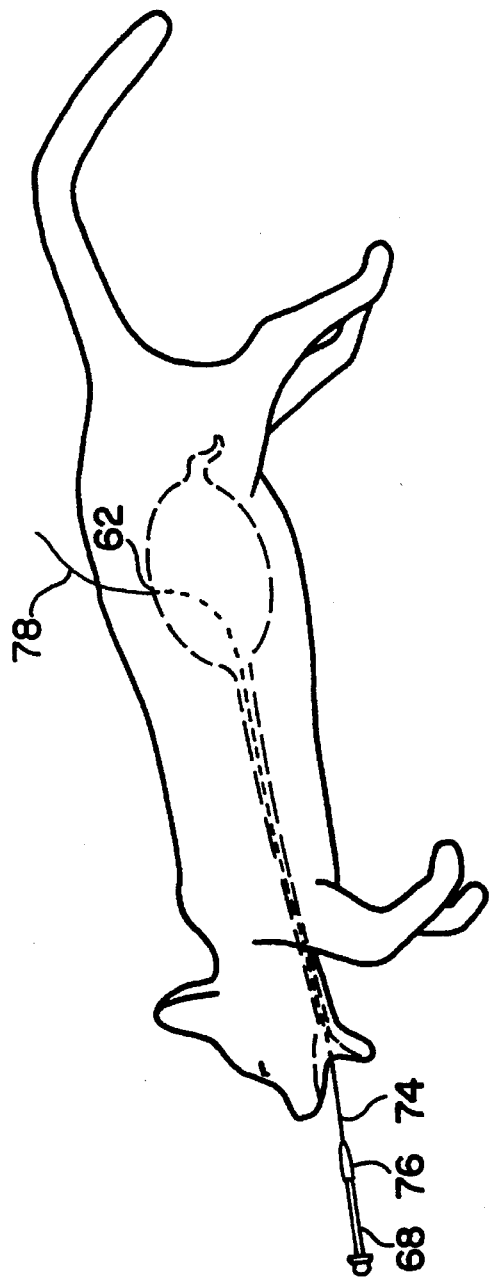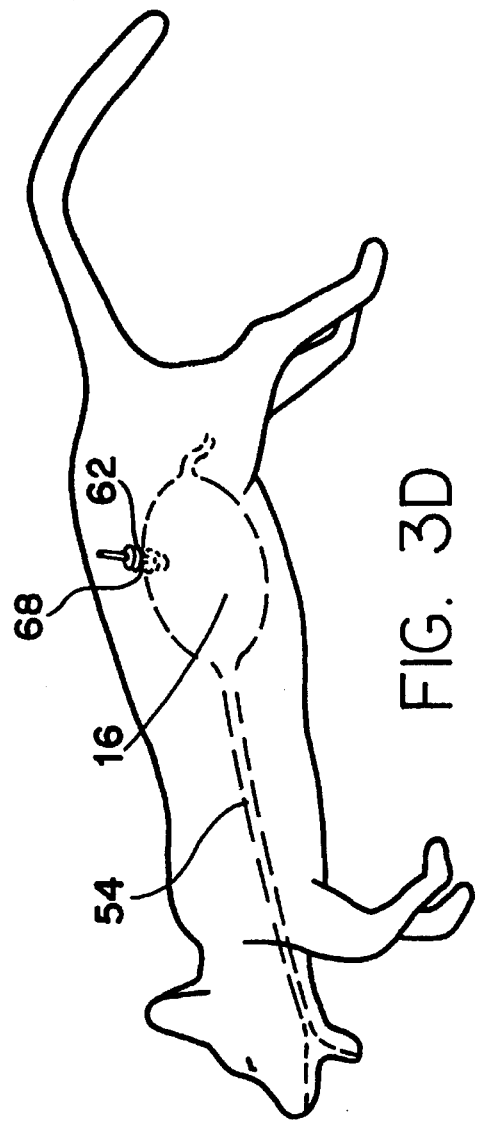

PERCUTANEOUS GASTROSTOMY FEEDING TUBE APPLICATOR AND METHOD.

This application is a continuation-in-part of U.S. application Ser. No. 08/068,905, filing date May 28, 1993, now abandoned.

BACKGROUND OF THE INVENTION

1. Technical Field

This invention relates generally to medical methods and apparatus and more specifically to procedures for forming a channel through a stomach wall in percutaneous gastrostomy.

2. Background Art

In recent years, the field of percutaneous gastrostomy has emerged in veterinary medicine as an effective technique for providing nutritional support for critically ill small animals. Animals that are malnourished or unwilling or unable to eat may benefit from this treatment, especially if nutritional support is needed for longer than about one week.

Percutaneous gastrostomy is a procedure involving the placement of a feeding tube through the skin, abdomen wall, and stomach wall of a patient as a means of supplying nutrients to the stomach without involving the head or esophagus. Percutaneous placement of the gastrostomy tube can be faster and involve less tissue trauma than the alternative of surgical placement, which involves making a grid incision through the skin and abdominal wall to locate and reach the stomach wall.

Percutaneous gastrostomy has been done in the past with the aid of an endoscope, which is a fiber-optic instrument that can be directed through the esophagus and into the stomach for viewing the inside of the stomach. The endoscope typically has a forceps extending through it and reaching to the distal end and a channel for delivery of gas or liquid to the vicinity of the distal end.

Percutaneous Endoscopic Gastrostomy (PEG) for veterinary patients is discussed in the article "Enteral Feeding of Critically Ill Pets: The Choices and Techniques," by P. Jane Armstrong, *Veterinary Medicine,* September 1992. Typically, the endoscope is introduced into the stomach and air is pumped through the endoscope to insufflate and distend the stomach. As the endoscopist views the inside of the stomach wall, an assistant chooses a point on the abdominal wall where the endoscope light can be clearly seen through the abdominal wall. The location of that point is confirmed by the assistant applying pressure to the abdominal wall and the endoscopist observing the resulting depression in the stomach wall. After good visualization of this point is confirmed, the assistant inserts a needle holding a suture strand through the skin, the abdominal wall, and stomach wall, creating a channel through these tissues. The endoscopist uses the endoscope forceps to grasp the strand and pulls the endoscope out of the stomach and esophagus and thus pulls the suture strand out through the patient's mouth.

The end of the suture strand exiting the mouth is attached to a pipette tip and then to a feeding tube such as a mushroom-shaped catheter. The pipette tip is usually threaded tip end first on to the suture strand to act as a smooth guide for the end of the feeding tube as it travels through the esophagus.

The end of the suture strand exiting the abdominal wall is pulled so that the pipette and feeding tube move through the esophagus, into the stomach, and into the channel through the stomach wall and abdominal wall. The suture strand and pipette may then be removed from the end of the feeding tube which exits from the abdominal skin. The feeding tube may be held in place by flanges, tape, or other anchoring devices. The feeding tube then serves as a conduit for nutritional supplements to flow into the stomach.

Thus, PEG involves locating the site for the channel by viewing the inside of the stomach and involves piercing into the abdominal wall and stomach wall from the outside of the body. PEG requires two people to perform the technique and requires an expensive endoscopic instrument.

Similar PEG techniques are used in human gastrostomy operations. Grobe (U.S. Pat. No. 5,112,310) discusses the "pull" PEG technique, which is similar to the veterinary technique described above. Grobe also discusses the similar "push" and "introducer" techniques and discloses apparatus for use in PEG. All these techniques involve the viewing of the inside of the stomach with an endoscope and an incision made from the outside toward the inside of the body and stomach.

Several U.S. patents disclose apparatus for use in PEG. Krol (U.S. Pat. No. 4,573,576) discloses a PEG kit. Picha et al. (U.S. Pat. No. 5,007,900) discloses a T-bar device for anchoring a catheter in the abdomen wall. Poirier et al. (U.S. Pat. No. 4,897,081) discloses a button-like device for anchoring a catheter.

Improved methods and devices, which are simple, reliable, and safe, are needed for placement of a percutaneous gastrostomy tube. Methods that can be done by one person are needed. Apparatus that is simpler and less expensive than an endoscope is needed.

DISCLOSURE OF INVENTION

The invented methods and apparatus allow percutaneous gastrostomy to be performed by a single person and without an endoscope. These methods and apparatus are especially useful in the field of veterinary medicine, because inexpensive and simple apparatus is preferred in veterinary clinics, and few of these clinics choose to invest in an endoscope. These invented methods and apparatus may also be useful in the field of human medicine, especially in areas or situations where the lack of personnel or lack of money for expensive equipment makes endoscope procedures difficult to perform.

The invented method includes the insertion of a device through the esophagus into the stomach so that the distal region is inside the stomach and the proximal region extends outside the mouth for access by the surgeon. The device has a removable needle near the distal region and this needle is shielded during the insertion into the stomach. The needle is placed in a desired location in the stomach near the stomach wall by manipulating the proximal region. The shield means is remotely actuated to uncover the needle and the needle is remotely actuated to move the needle forward to pierce through the stomach wall and abdomen wall to reach the outside of the body. The needle may be remotely actuated to move backward to retract back into the stomach. Thus, the invented method cuts or pierces a channel from the inside of the stomach to the outside of the body. The channel may be used for receiving a suture strand, a feeding tube, or other apparatus and may be used for other access of the stomach.

The step of placing the needle in the desired location may include the procedure of tapping a blunt end of the device against the stomach wall so that the tapping may be palpated or felt on the outside of the body. Because the blunt end is a predetermined distance and location relative to the needle, this tapping is used to indicate where the blunt end is located inside the stomach and therefore where the needle is located inside the stomach.

Optionally, the method may include attaching a suture strand to the needle after the needle pierces through to the outside of the body and remotely actuating the needle to move backward into the stomach to pull the suture strand through the channel and into the stomach. Optionally, the method may include pulling the device out of the stomach and esophagus to pull the suture strand out through the esophagus and mouth for attachment to a feeding tube or other apparatus. The end of the suture strand exiting the channel may then be pulled to move the feeding tube or other apparatus through the esophagus and the stomach and into the channel.

The applicator device invented for this procedure has an elongated body with a distal region and a proximal region. The device includes a removable needle, a shield means, and an actuating means. The shield means is for covering the needle to prevent damage to the mouth, esophagus, and stomach when the needle in being inserted into the stomach. The actuating means is for remotely moving the needle forward to pierce through the body tissue and backward to retract into the stomach.

The elongated body of the device may comprise a probe, with a distal region having a blunt end, and a rod that is generally parallel to and slidably attached to the probe. The removable needle may be attached to the distal region of the rod so that it slides forward and backward, relative to the blunt end, to pierce the stomach wall and abdomen wall and to retract away from the stomach wall, respectively. Optionally, the probe may be a hollow tube with open ends, and the rod may be slidably received inside the tube.

BRIEF DESCRIPTION OF THE DRAWINGS

FIG. 1A is a side view of one embodiment of the invented device, with the removable needle in the retracted position.

FIG. 1B is a side view of the embodiment of FIG. 1A, with the needle actuated into the extended position.

FIG. 2A is a detailed view of the removable needle and the distal regions of the probe and rod from the embodiment of FIGS. 1A and 1B.

FIG. 2B is a cross-sectional view of the probe and rod from FIG. 2A, as viewed along the lines 2B—2B.

FIGS. 3A-3D illustrate the steps of one mode of the invented method, using the device of FIGS. 1A and 1B.

FIG. 3A shows the device inserted through the esophagus and into the stomach, with the blunt end tapping against the stomach wall to properly locate the needle.

FIG. 3B shows the needle actuated forward, piercing a channel through the stomach wall and abdomen wall, extending outside the body, and receiving a suture strand.

FIG. 3C shows the suture strand pulled through the esophagus, attached to a feeding tube and pipette, and ready to be pulled through the stomach and into the channel.

FIG. 3D shows the feeding tube anchored in place after being pulled into the channel and ready for use as a conduit for nutritional support.

BEST MODE FOR CARRYING OUT INVENTION

Figure 2C:
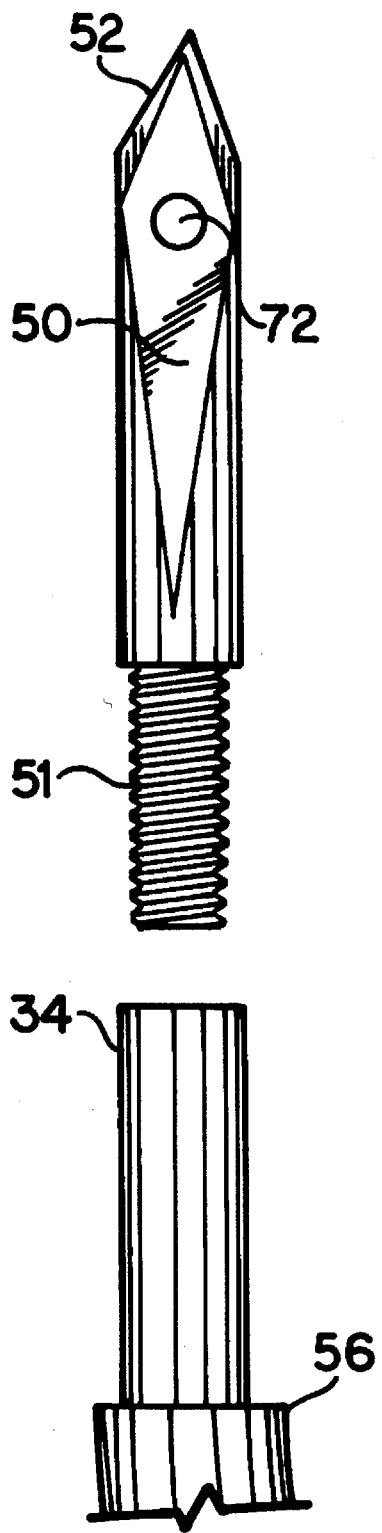
FIG. 2C is a view similar to 2A showing how the removable needle is attached to the rod in the preferred embodiment.
Figure 4:
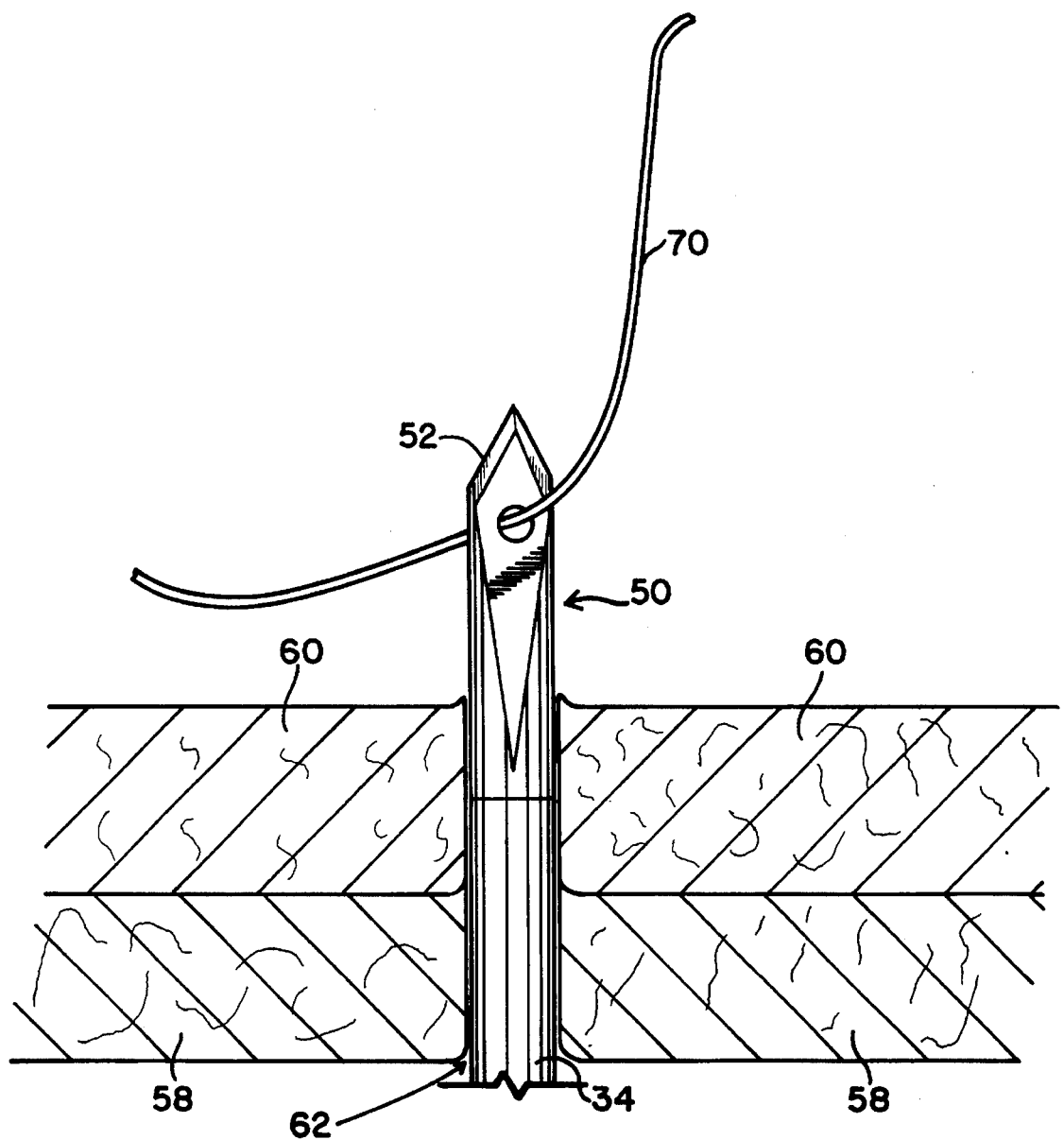
FIG. 4 is a cross-sectional view of the stomach and abdomen walls, with the needle of FIG. 3B piercing the channel and receiving the suture strand.

Referring to FIGS. 1–4, there are shown the preferred but not the only embodiments of the invented device and method. The gastrostomy device 10 has an elongated body, which has a distal region 14 for extending into the patient's stomach 16, and a proximal region 18 for extending out from the patient's mouth 20.

In the preferred embodiment, the elongated body comprises an elongated rod 30 and an elongated probe, which is a tube 32. The rod 30 has a distal region 34 and a proximal region 36, and the tube 32 has a distal region 38 and a proximal region 40. The tube 32 has a hollow interior 42 and open ends that are referred to as the opening 44 at the distal region 38 and the aperture 46 at the proximal region 40. The rod 32 may be slidably received inside the tube 32, so that the rod distal region 34 may slide forward and backward through the opening 44 and the rod proximal region 36 may slide forward and backward through the aperture 46. The terms "forward" and "front" mean toward or past the distal region 38 of the tube 32 and the terms "backward" and "in back of" mean toward or past the proximal region 40 of the tube 32.

A removable needle 50 is attached to the distal region 34 of the rod 32 and 50 is removable and re-attachable for easy cleaning, autoclaving, sharpening, or replacement. Removable needle 50 can be attached to rod 32 by any conventional means, such as a bayonet mount or friction fit. Here needle 50 has threaded extension 51 for threadable engagement in distal region 34 of rod 32. The preferred needle 50 is a narrow arrow-head shape, with a V-shaped cutting edge 52 oriented with the cutting edge 52 facing generally distally and generally parallel to the longitudinal axis of the device 10. Other shapes and orientations may be used to optimize the cutting edge 52 for a particular application. A thin, sewing-needle shape or a scalpel-shaped blade could be used. The cutting edge 52 could face distally but at a 45° angle, for example, to the longitudinal axis of the device 10. The limitation is that the needle 50 should be a shape and orientation that allows it to be shielded to fit through the mouth 20, esophagus 54, and into the stomach 16.

The proximal region 36 of the rod 30 extends back past the proximal region 40 of the tube 32 so that the surgeon may access and push the rod 30 forward to slide the removable needle 50 to an extended position and pull the rod backward to slide the needle 50 to a retracted position. When pushed forward, the distal region 34 of the rod 30 and the needle 50 extend out from the opening 44 and in front of the blunt end 56 of the tube 32, thus becoming unshielded and exposed. When the blunt end 56 of the tube 32 has been placed in a desired location against the stomach wall 58, this pushing of the rod 30 and needle 50 forward acts to force the needle 50 through the stomach wall 58 and abdomen wall 60, piercing a channel 62 through these tissues. Therefore, grasping the rod proximal region 36 or optional handle 64 and the tube proximal region 40 or optional grip 65 and pushing the rod 30 forward relative to the tube 32 is both the preferred way of actuating the shield means to unshield the needle 50 and the preferred way of actuating the needle 50 to move forward to pierce the channel. In the preferred embodiment and preferred method, the tube distal region 38 acts as the retractable shield means, because it covers the removable needle 50 during the insertion through the esophagus 54 and, in effect, retracts from the needle 50 when the needle 50 is pushed forward. Thus, the rod proximal region 36, tube proximal region 40, and slidably connection between the rod 30 and tube 32 cooperate to act as the actuating means for moving the needle 50 forward and backward.

Alternatively, other designs for the gastrostomy device 10 may be used. For example, the rod could be slidably connected parallel and beside, but not inside, the probe. In such an embodiment, a shield plate could be attached to the probe in such a way that it extends to cover the removable needle during insertion through the esophagus but allows the needle to slide forward and out from under the plate when the rod is pushed. Another shield means for this embodiment could be a hinged shield plate that is biased to cover the removable needle until the needle pushes the plate out of the way when the rod is pushed forward. In another embodiment, the probe could have the needle and a hinged shield attached to its distal end and have linkage extending through or beside the probe for actuating the hinged shield to unshield the needle. In such an embodiment, after the unshielding of the needle, the proximal region of the probe would be pushed forward to actuate the needle to pierce a channel in the stomach and abdomen walls. Thus, the actuating means may be as simple as the surgeon pushing the device forward into the tissue.

In another embodiment, the gastrostomy device may include or be a part of an endoscope. The elongated body may slide through a channel in the endoscope. Such embodiment allows viewing of the inside of the stomach, which is beneficial in human gastrostomy.

Preferably, a biasing means is included in the device 10 for biasing the rod 30 backwards relative to the tube 32, so that the needle 50 is shielded except when the surgeon purposely pushes the rod 30 forward. In the preferred embodiment, the biasing means is a coiled spring 66, which extends to force apart the rod handle 64 and the tube proximal region 40.

The elongated body of the device 10 may be of various degrees of flexibility, ranging from rigid to somewhat flexible for allowing some bending when significant force is placed on the device 10. Embodiments that are somewhat flexible may aid in making easier the insertion of the device 10 through the esophagus 54, however, flexibility should be limited to a degree that assures efficient and confident placement of the needle 50 without buckling, bending, or crimping of the device 10.

In the preferred embodiment, the tube 32 is rigid and curved, resulting in the tube distal region 38 and tube proximal region 40 lying at an obtuse angle, of preferably, but not limited to, about 130°–150° to each other. This curve is slight enough and gradual enough to allow easy insertion of the device 10 through the esophagus 54 but also is great enough to allow easy pointing of the blunt end 56 toward the front or side of the stomach 16, which are the preferred locations for the channel 62 for a gastrostomy feeding tube 68. In embodiments having a curve, the rod 30 should be flexible enough to follow the curve of the tube 32 when pushed and pulled but rigid enough to prevent buckling or bending that would bind the rod 30 inside the tube 32 or interfere with the needle 50 piercing through the stomach wall 58 and abdomen wall 60.

The invented gastrostomy method involves making the channel through the stomach and abdomen walls 58,60 from the inside out, as discussed in the above description of the invented device. The method may be used to make the channel 62 for various medical uses, including the insertion of a feeding tube 68 or other catheter.

The preferred method involves tapping the blunt end 56 against the stomach wall 58 to determine when the blunt end 56 and therefore the needle 50 are in a desirable location for piercing the channel 62. The surgeon or veterinarian may palpate the tapping from the outside of the patient's body to accurately confirm the location of blunt end 56 and needle 50 before actuating the needle 50 to pierce the channel 62. Thus, the invented method provides a simple, accurate, and quick way of piercing the channel 62 without expensive equipment and without the assistance of a second person.

The method may optionally include other steps. A suture strand 70 or other elongated string may be attached to the needle 50, for example, by threading the strand 70 through the eye 72 of the needle 50. The use of the term "suture strand" is not intended to limit the strand 70 to a particular design or material. The needle 50 may be actuated backwards to draw the first end 74 of the suture strand 70 back into the stomach 16 and the device 10 may be pulled out of the esophagus 54 to draw the first end 74 out of the mouth 20. The first end 74 may be attached to a pipette 76 and feeding tube 68, as is done in the other gastrostomy techniques discussed in the above section "Background Art." The pipette 76 and feeding tube 68 may then be drawn into the channel 62 by pulling the second end 78 of the strand 70. The feeding tube 68 may then be anchored in place and used for nutritional support as described in the "Background Art" section and the P. Jane Armstrong article.

The preferred materials for the invented device are stainless or surgical steel. Other materials that fulfill the sterility, strength and piercing requirements may also be used.

While there is shown and described the present preferred embodiment of the invention, it is to be distinctly understood that this invention is not limited thereto but may be variously embodied to practice within the scope of the following claims.

I claim:

1. A gastrostomy method for making a channel through a patient's stomach wall and abdomen wall for receiving a suture strand with first and second ends and for receiving a feeding tube, the gastrostomy method comprising the steps of:

directing an elongated gastrostomy device through the patient's esophagus and into the stomach, the device having a proximal region and a distal region, lying at an obtuse angle within the range of 130° to 150° to the proximal region for placement in the stomach, an opposing proximal region for placement outside the esophagus for access by the surgeon, a removable needle near the distal region for piercing the channel, and a shield means for covering the needle when it is being directed through the esophagus, placing the needle in a desired location near the stomach wall by manipulating the proximal region of the device, remotely actuating the shield means to unshield the needle, remotely actuating the needle to move forward to make the channel by piercing through the stomach wall and abdomen wall to extend outside the patient's body.

2. A gastrostomy method as set forth in claim 1, wherein the gastrostomy device comprises an elongated probe and an elongated rod generally parallel to and slidably connected to the probe, the probe having a proximal region and a distal region with a blunt end, and the rod having a proximal region and a distal region attached to the removable needle.

3. A gastrostomy method as set forth in claim 2, wherein the step of placing the needle in the desired location comprises moving and tapping the blunt end against the stomach wall so that the tapping may be felt on the outside of the body wall.

4. A gastrostomy method as set forth in claim 2, wherein the step of remotely actuating the shield means comprises pushing the rod proximal region forward to slide the needle forward and away from the shield means.

5. A gastrostomy method as set forth in claim 2, wherein the step of actuating the needle to move forward comprises pushing the rod proximal region forward to slide the needle forward parallel to the probe distal region and in front of the blunt end.

6. A gastrostomy method as set forth in claim 1, further comprising the step of securing the first end of the suture strand to the needle after the needle is actuated forward and is extending outside the body.

7. A gastrostomy method as set forth in claim 6, further comprising the step of actuating the needle to move backward to draw the first end of the suture strand through the abdomen wall and stomach wall and into the stomach.

8. A gastrostomy method as set forth in claim 7, further comprising the step of pulling the device out of the esophagus so that the needle draws the first end of the suture strand out through the esophagus and leaves the second end of the suture strand extending through the channel and outside the abdomen wall.

9. A gastrostomy method as set forth in claim 8, further comprising the steps of attaching the first end of the suture strand to the feeding tube and pulling the second end of the suture strand to move the feeding tube through the esophagus and stomach and into the channel.

10. A gastrostomy device for making a channel through a patient's stomach wall and abdomen wall for receiving a suture strand and a feeding tube, the gastrostomy device comprising:

an elongated body having a distal region and an opposing proximal region, with the distal region lying at an obtuse angle within the range of 130° to 150° to the proximal region the distal region for placement through the patient's esophagus into the stomach and the proximal region for extending out of the esophagus for access by the surgeon, a removable needle attached to the elongated body distal region for making the channel by piercing through the stomach wall and abdomen wall to extend outside the patient's body, a retractable shield means for covering the needle when the distal region is moved through the esophagus and for being remotely retracted to uncover the needle, an actuating means accessible from outside the esophagus for remotely moving the needle forward to pierce the channel.

11. A gastrostomy device as set forth in claim 10, wherein the elongated body comprises:

an elongated probe having a proximal region and an opposing distal region having a blunt end for tapping against the stomach wall, and an elongated rod extending generally parallel to and slidably connected to the probe and having a proximal region and an opposing distal region attached to the removable needle.

12. A gastrostomy device as set forth in claim 11, wherein the probe is obtusely curved and the rod is flexible for slidably following the curve of the probe.

13. A gastrostomy device as set forth in claim 11, further comprising a biasing means for biasing the rod backwards relative to the probe to pull the needle end behind the blunt end of the probe.

14. A gastrostomy device as set forth in claim 11, wherein the probe comprises a tube having a hollow interior and an opening near the blunt end and an aperture near the back region.

15. A gastrostomy device as set forth in claim 14, wherein the rod is slidably received in the tube hollow interior so that the needle may slide forward and backward through the opening and the rod handle may be accessed through the aperture.

16. A gastrostomy device for making a channel through a patient's stomach wall and abdomen wall for receiving a suture strand and a feeding tube, the gastrostomy device consisting of:

an elongated probe having a proximal region and an opposing distal region, lying at an obtuse angle within the range of 130° to 150° to the proximal region having a blunt end for tapping against the stomach wall, an elongated rod extending generally parallel to and slidably connected to the probe and having a proximal region and an opposing distal region, a removable needle attached to the distal region of the rod for making the channel by piercing through the stomach wall and abdomen wall to extend outside the patient's body, a retractable shield means for covering the needle when the distal region is moved through the esophagus and for being remotely retracted to uncover the needle, and an actuating means accessible from outside the esophagus for remotely moving the needle forward to pierce the channel.

17. A gastrostomy device as set forth in claim 16, wherein the probe is obtusely curved and the rod is flexible for slidably following the curve of the probe.

18. A gastrostomy device as set forth in claim 16, wherein the probe comprises a tube having a hollow interior and an opening near the blunt end and an aperture near the back region.

19. A gastrostomy device as set forth in claim 18, wherein the rod is slidably received in the tube hollow interior so that the needle may slide forward and backward through the opening and the rod handle may be accessed through the aperture.

* * * * *